United States Patent
Dietrich et al.

(10) Patent No.: US 9,689,783 B2
(45) Date of Patent: Jun. 27, 2017

(54) Z-AXIS TEST COUPON STRUCTURE AND METHOD FOR ADDITIVE MANUFACTURING PROCESS

(71) Applicant: The Boeing Company, Chicago, IL (US)

(72) Inventors: David M. Dietrich, St. Peters, MO (US); Michael W. Hayes, Belleville, IL (US)

(73) Assignee: The Boeing Company, Chicago, IL (US)

( * ) Notice: Subject to any disclaimer, the term of this patent is extended or adjusted under 35 U.S.C. 154(b) by 167 days.

(21) Appl. No.: 14/795,528

(22) Filed: Jul. 9, 2015

(65) Prior Publication Data

US 2015/0308935 A1    Oct. 29, 2015

Related U.S. Application Data

(62) Division of application No. 12/772,619, filed on May 3, 2010, now Pat. No. 9,109,979.

(Continued)

(51) Int. Cl.
*G01N 3/08* (2006.01)
*B29C 67/00* (2017.01)
(Continued)

(52) U.S. Cl.
CPC ........... *G01N 3/08* (2013.01); *B29C 67/0092* (2013.01); *B22F 2003/1058* (2013.01);
(Continued)

(58) Field of Classification Search
CPC .................. G01N 3/08; B29C 67/0092; B22F 2003/1058
See application file for complete search history.

(56) References Cited

U.S. PATENT DOCUMENTS 3,993,817 A   11/1976  Schultz
5,284,063 A    2/1994  Newell
(Continued)

FOREIGN PATENT DOCUMENTS

DE   WO 2009010034 A2 *  1/2009  ............ B22F 1/0059
EP         1486317           8/2008

OTHER PUBLICATIONS

European Patent Office. "Extended European Search Report," issued in connection with Application No. 10193278.8, May 9, 2014, 3 pages.

(Continued)

*Primary Examiner* — Jill Warden
*Assistant Examiner* — Matthew Krcha
(74) *Attorney, Agent, or Firm* — Hanley, Flight & Zimmerman, LLC (57) ABSTRACT

A Z-axis test coupon structure and method for additive manufacturing process are disclosed. An example method of fabricating Z-axis test coupons for additive manufacturing processes, includes fabricating tensile specimens, the fabricating of the tensile specimens including providing a web between adjacent ones of the tensile specimens, and the fabricating of the tensile specimens including using an additive manufacturing process, removing the web from between the adjacent ones of the tensile specimens, and testing a tensile strength of one of the tensile specimens.

14 Claims, 9 Drawing Sheets

Related U.S. Application Data (60) Provisional application No. 61/266,301, filed on Dec. 3, 2009.

(51) Int. Cl.

| | | |
|---|---|---|
| B22F 3/105 | (2006.01) | |
| B33Y 10/00 | (2015.01) | |
| B33Y 50/00 | (2015.01) | |

(52) U.S. Cl.
CPC ............... *B33Y 10/00* (2014.12); *B33Y 50/00* (2014.12); *G01N 2203/0282* (2013.01); *G01N 2203/0476* (2013.01); *Y10T 428/21* (2015.01); *Y10T 428/216* (2015.01)

(56) References Cited

U.S. PATENT DOCUMENTS

| | | | |
|---|---|---|---|
| 6,383,687 B1 | 5/2002 | Gibbons et al. | |
| 6,450,393 B1* | 9/2002 | Doumanidis | B23P 15/00 156/264 |
| 2006/0070452 A1 | 4/2006 | Bohlmann et al. | |
| 2008/0241392 A1* | 10/2008 | Dimter | B22F 3/1055 427/256 |
| 2011/0137578 A1 | 6/2011 | Dietrich et al. | |
| 2012/0113439 A1* | 5/2012 | Ederer | B22F 1/0059 358/1.9 |

OTHER PUBLICATIONS

Tong et al., "An Improved Technique for Tensile Testing of Sheet Metals," Jun. 2-5, 2008, 2 pages, Proceedings of the XIth International Congress and Exposition, Society for Experimental Mechanics Inc., Orlando, Florida USA.
Ahn et al., "Anisotropic tensile failure model of rapid prototyping parts—fused deposition modeling (FDMTM)," International Journal of Modern Physics B, vol. 17, Nos. 8 and 9, 2003, p. 1510-1516.
Ahn et al., "Anisotropic material properties of fused deposition modeling ABS," Rapid Prototyping Journal, vol. 8, No. 4, 2002, p. 248-257.
Agarwala et al., "Structural Quality of Parts Processed by Fused Deposition," Rapid Prototyping Journal, vol. 2, No. 4, 1996, pp. 4-19.
Baker et al., "Composite Materials for Aircraft Structures 2nd Edition," p. 174, American Institute of Aeronautics and Astronautics, 2004.
Bernard et al., "Evolutions of Rapid Product Development with Rapid Manufacturing: Concepts and Applications," International Journal of Rapid Manufacturing, vol. 1, No. 1, 2009, pp. 3-17.
Bourell et al., "Roadmap for Additive Manufacturing—Identifying the Future of Freeform Processing," Roadmap for Additive Manufacturing Workshop: Identifying the Future of Freeform Processing, University of Texas at Austin, pp. 1-92, 2009.
Comb et al., "Layered manufacturing control parameters and material selection criteria," Manufacturing Science and Engineering, vol. 2, ASME 1994, p. 547-556.
Fowlkes et al., "Engineering Methods for Robust Product Design," 1995, p. 69, Addison-Wesley.
Kotlinski et al., "Dimensional Deviations of Machine Parts Produced in Laser Sintering Technology," International Journal of Rapid Manufacturing, vol. 1, No. 1, 2009, pp. 88-98.
Kridli et al., "Rapid Prototyping: Theory and Practice," 2006, 24 pages, 1st Edition, Springer.
Kulkarni et al., "Deposition Strategies and Resulting Part Stiffness in Fused Deposition Modeling," Journal of Manufacturing Science and Engineering, vol. 121, ASME 1999, p. 93-103.
Liou, "Rapid Prototyping and Engineering Applications: A Toolbox for Prototype Development," (Dekker Mechanical Engineering), CRC Press, Sep. 2007, 26 pages.
Montero et al., "Material Characterization of Fused Deposition Modeling (FDM) Process," Proc. of Rapid Prototyping and Manufacturing Conference, Society of Manufacturing Engineers, May 15-17, Cincinnati, OH, 2001, 1 page.
Pandey et al. "Improvement of surface finish by staircase machining in fused deposition modeling," Journal of Materials Processing Technology, vol. 132, Sep. 24, 2002, p. 323-331.
Rodriguez et al., "Design of Fused-Deposition ABS Components for Stiffness and Strength," Journal of Mechanical Design, vol. 125, ASME 2003, p. 545-551.
Ruffo, "The impact of rapid manufacturing on business management," Dissertation for Loughborough University, 2006, p. 65.
Strong, "Fundamentals of Composites Manufacturing: Materials, Methods and Applications," Society of Manufacturing Engineers, 2008, pp. 5-8.
Walter et al, "Rapid Manufacturing and its impact on Supply Chain Management," Proceedings of the Logistics Research Network Annual Conference, Dublin, Ireland, Sep. 9-10, 2004, 12 pages.
United States Patent and Trademark Office, "Non-Final Office Action," issued in connection with U.S. Appl. No. 12/772,619, May 28, 2013, 14 pages.
United States Patent and Trademark Office, "Final Office Action," issued in connection with U.S. Appl. No. 12/772,619, Aug. 15, 2013, 9 pages.
United States Patent and Trademark Office, "Advisory Action," issued in connection with U.S. Appl. No. 12/772,619, Nov. 25, 2013, 5 pages.
United States Patent and Trademark Office, "Notice of Allowance," issued in connection with U.S. Appl. No. 12/772,619, Mar. 24, 2015, 22 pages.
United States Patent and Trademark Office, "Notice of Allowance," issued in connection with U.S. Appl. No. 12/772,619, Jul. 9, 2015, 19 pages.
"Standard Test Method for Tensile Properties of Plastics," 16 pages, American Society for Testing and Materials, Annual Book of ASTM Standards—D638-08, May 2008.

\* cited by examiner

Z-AXIS TEST COUPON STRUCTURE AND METHOD FOR ADDITIVE MANUFACTURING PROCESS

This patent arises from a divisional of U.S. patent application Ser. No. 12/772,619, filed May 3, 2010, and claims the benefit of U.S. Provisional Patent Application No. 61/266,301, filed Dec. 3, 2009. The entireties of U.S. Provisional Patent Application No. 61/266,301 and U.S. patent application Ser. No. 12/772,619 are incorporated herein by reference.

TECHNICAL FIELD

The disclosure relates to additive manufacturing processes. More particularly, the disclosure relates to a Z-axis test coupon structure and a quick and repeatable method for producing Z-axis (vertical) test coupons in additive manufacturing processes that require support structure, with related methods of use.

BACKGROUND

Additive Manufacturing (AM) encompasses a variety of forms to cover an entire range of quick-response direct fabrication, typically in a layered format, of end-use articles. These end use articles generally exhibit high geometric customization, such as hearing aids, dental implants and customized applications. In addition, AM may also exhibit relatively low production volume for applications residing in formula car racing, aerospace and medical industries, for example and without limitation.

AM technologies have proven their capabilities for mass-customized production in different domains. The robustness of these technologies has not completely been demonstrated in a mass production context. In aerospace applications, mechanical property performance is important. The end-use parts fabricated using AM must meet the requirements of the design engineer. A common type of additive manufacturing process is known as fused Deposition Modeling (FDM).

Fused Deposition Modeling (FDM) is an extrusion-based process that feeds material in solid wire form and then melts it into a shape and forms a solid. FDM is a nonlaser filament extrusion process that may utilize engineering thermoplastics, which may be heated from filament form and extruded in very fine layers to build each model from the bottom up. The models may be made from acrylonitrile butadiene styrene (ABS), polycarbonate, polyphenylsulfone (PPSF), and various versions of these materials. Furthermore, in many cases, the models may be tough enough to perform functional tests. The material used is fed into an extrusion head in solid wire form and then liquefied in the extrusion head and deposited through a nozzle in liquid form. The extrusion head is able to move in the X-Y plane and is controlled to deposit very thin beads of molten material onto the build platform to form the first layer.

Aerospace and other applications may demand that rigorous testing and certification be carried out preparatory to using materials and processes for the manufacture of components. Moreover, specific material requirements may be associated with the part candidates for aircraft and other structures. In order for additive manufacturing to become fully adopted as a credible manufacturing process, it may be necessary to organize a path that provides a roadmap to production for candidate parts that are inclined to become AM candidate parts.

For FDM and other additive manufacturing processes such as SLS (Selective Laser Sintering), Z axis orientation of parts may be generally weaker than both X and Y directions of the parts. This Z axis limiting effect may be due primarily to the additive nature inherent in most all RM processes. Due to the Z axis limitation, design engineers may limit the technology to the weakest anisotropic plane and place emphasis on Z axis testing. This emphasis on Z axis testing may be relevant for many testing types. Due to budget constraints, industry may focus on one or two types of testing techniques that simulate physical conditions of applications and a large population of samples. This constraint has lead to an overall decision to test for both uniaxial tensile and flexural tests.

The additive manufacturing industry does not currently have a standard for building Z-axis (vertical) tensile bar coupons for processes that require support material. Therefore, a Z-axis test coupon structure and a quick and repeatable method for producing Z-axis (vertical) test coupons in additive manufacturing processes that require support structure are needed.

SUMMARY

The disclosure is generally directed to a Z-axis test coupon structure. An illustrative embodiment of the Z-axis coupon structure includes a plurality of circularly-arranged tensile specimens oriented along a Z-axis and at least one web connecting adjacent ones of the plurality of tensile specimens.

The disclosure is further generally directed to a method of fabricating standardized Z-axis test coupons for additive manufacturing processes. An illustrative embodiment of the method includes initiating fabrication of tensile specimens, providing at least one web between the tensile specimens, completing fabrication of the tensile specimens, removing the at least one web from between the tensile specimens and testing a tensile strength of the tensile specimens.

The disclosure is further generally directed to a method of developing consistent material allowables for additive manufacturing. An illustrative embodiment of the method includes providing a Z-axis coupon structure having a circular arrangement of tensile specimens; providing a set of material deposition control paths for the Z-axis coupon structure; assessing signal factors, noise factors and control factors of the Z-axis coupon structure; optimizing material laydown for maximum tensile strength of a production part based on the signal factors, the noise factors and the control factors; and developing a statistical allowables database for the production part by testing the tensile specimens.

The disclosure is also generally directed to a method to use the test coupon mechanical property evaluation data as a unique additive modeling Part Candidate selection method. These parts are generally highly complex, low quantity geometries that may be polymer based. They are typically difficult to construct using conventional manufacturing solutions. In addition, assembly integration, or the ability to combine several parts into a single part is taken into account during part selection. The unique elements of the FDM process compared to features of functional part candidates will indicate advantages of using one build method over another for each element trait. For an FDM candidate, each element shares a common theme that leverages a need for complex geometry that may be difficult or impossible to construct using conventional manufacturing technology.

In some embodiments, the Z-axis test coupon structure may include fourteen circularly-arranged tensile specimens oriented along a Z-axis and oriented at various angles with respect to at least one tool path direction. Each of the tensile specimens may include a generally elongated middle section and a lower grip and an upper grip provided at respective ends of the middle section. Orientation text may be provided on at least one of the lower grip and the upper grip. A lower web may connect adjacent ones of the plurality of tensile specimens and have a generally flat upper edge and a generally notched lower edge. An upper web may connect adjacent ones of the plurality of tensile specimens and have a generally flat upper edge and a generally notched lower edge.

In some embodiments, the method of fabricating standardized Z-axis test coupons for additive manufacturing processes may include initiating fabrication of tensile specimens each having a generally elongated middle section, a lower grip and an upper grip provided at respective ends of the middle section and orientation text provided on at least one of the lower grip and the upper grip; providing an upper web and a lower web each having a generally flat upper edge and a generally notched lower edge between the tensile specimens; completing fabrication of the tensile specimens; fabricating a production part simultaneously with initiating fabrication of the tensile specimens; defining at least one tool path orientation in the tensile specimens; removing the at least one web from between the tensile specimens; and testing a tensile strength of the tensile specimens.

In some embodiments, the method of developing consistent material allowables for additive manufacturing may include providing a Z-axis coupon structure having a circular arrangement of tensile specimens each having a generally elongated middle section and a lower grip and an upper grip at respective ends of the middle section and an upper web and a lower web between the tensile specimens and each having a generally flat upper surface and a generally notched lower surface; providing a set of material deposition control paths for the Z-axis coupon structure; assessing signal factors, noise factors and control factors of the Z-axis coupon structure; optimizing material laydown for maximum tensile strength of a production part based on the signal factors, the noise factors and the control factors; and developing a statistical allowables database for the production part by testing the tensile specimens. This database provides and supports a methodology for selecting candidate FDM parts

BRIEF DESCRIPTION OF THE ILLUSTRATIONS

The disclosure will now be made, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
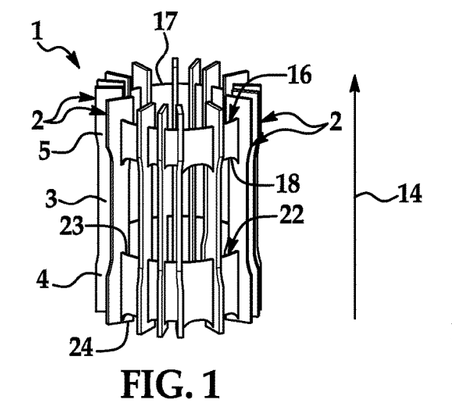
FIG. 1 is a perspective view of an illustrative embodiment of the Z-axis test coupon structure.
Figure 2:
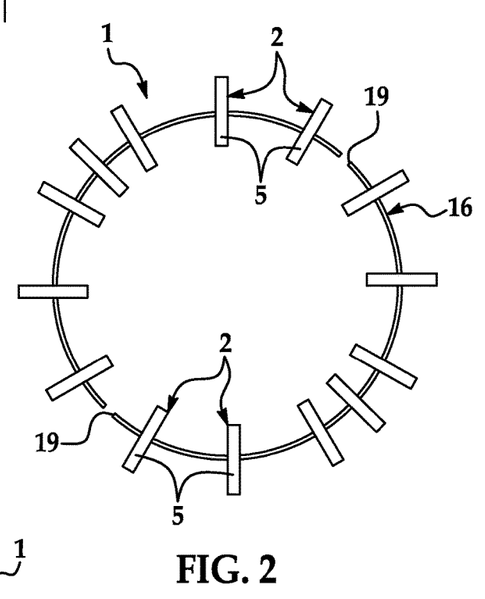
FIG. 2 is a top view of an illustrative embodiment of the Z-axis test coupon structure, more particularly illustrating breakaway bracing of tensile specimens in the Z-axis test coupon structure.
Figure 3:
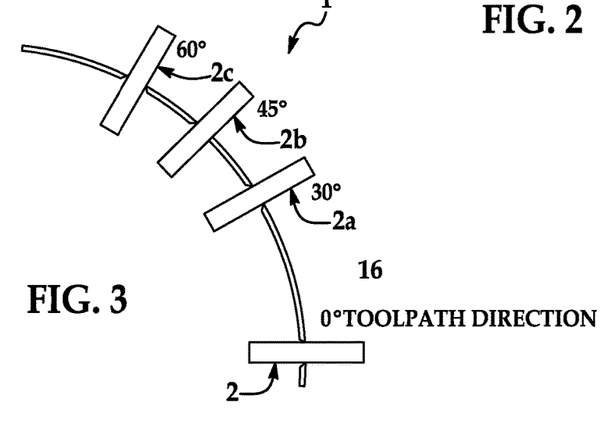
FIG. 3 is a top view, partially in section, of an illustrative embodiment of the Z-axis test coupon structure, more particularly illustrating angular orientation of the tensile specimens with respect to a tool path direction.
Figure 4:
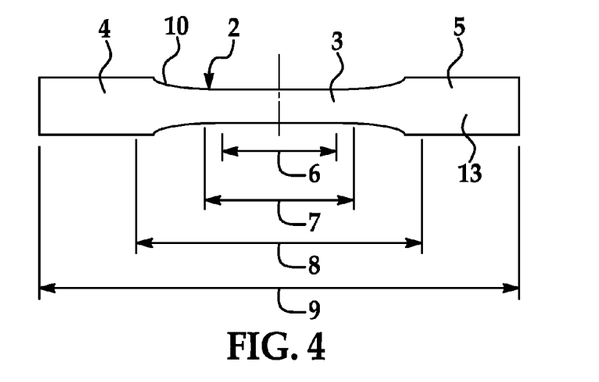
FIG. 4 is a callout diagram illustrating dimensions and structure of a tensile specimen of an illustrative embodiment of the Z-axis test coupon.
Figure 4A:
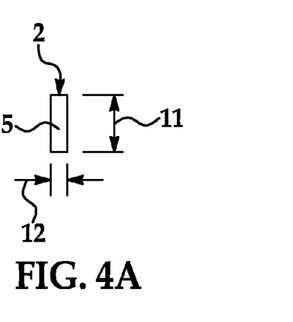
FIG. 4A is an end view of the tensile specimen of FIG. 4.

Referring to FIGS. 1-4, an illustrative embodiment of the Z-axis test coupon structure is generally indicated by reference numeral 1 in FIG. 1. The Z-axis test coupon structure 1 may include a grouping of multiple ASTM D638 Type I test coupons or tensile specimens 2 oriented in the Z direction 14. In some embodiments, the Z-axis coupon structure 1 may include at least five tensile specimens 2. In some embodiments, the Z-axis coupon structure 1 may include fourteen tensile specimens 2, as shown. Each tensile specimen 2 may be constructed from any fused deposition modeling (FDM) material. As shown in FIG. 4, in some embodiments, each tensile specimen 2 may have a generally elongated middle section 3 and a lower grip 4 and an upper grip 5 at respective ends of the middle section 3. In some embodiments, the middle section 3 may be narrower than the lower grip 4 and the upper grip 5. As further shown in FIG. 4, the middle section 3 of each tensile specimen 2 may have a gage length 6 of about 50 mm. The length 7 of the middle section 3 may be about 57 mm. The distance 8 between the lower grip 4 and the upper grip 5 may be about 115 mm. The overall length 9 of the tensile specimen 2 may be about 165 mm. The fillet radius 10 of each tensile specimen 2 may be about 76 mm. As shown in FIG. 4A, the overall width 11 of each of each tensile specimen 2 may be about 19 mm. The overall thickness 12 of each tensile specimen 2 may be less than or equal to about 7 mm.

At least one web 16, 22 may connect the tensile specimens 2 to each other in the Z-axis test coupon structure 1. In some embodiments, an upper web 16 and a lower web 22 may connect the tensile specimens 2 to each other. The upper web 16 and the lower web 22 may be made of the parent material from which the tensile specimens 2 are fabricated. Each of the upper web 16 and the lower web 22 may generally have a circular ring shape and may be removable from the tensile specimens 2 upon completion of fabrication of the Z-axis test coupon structure 1 at web breaks 19, as shown in FIG. 2.

As shown in FIG. 1, in some embodiments, the upper web 16 of each Z-axis test coupon 1 may have a generally flat upper edge 17 and a generally arched or notched lower edge 18. Likewise, the lower web 22 may have a generally flat upper edge 23 and a generally arched or notched lower edge 24. As shown in FIG. 3, the circularly-arranged tensile specimens 2 in the Z-axis test coupon structure 1 may be oriented at various degrees with respect to at least one tool path direction or geometry in the Z-axis test coupon structure 1. In the example shown in FIG. 3, the tensile specimen 2 is oriented at a 0 degree angle with respect to a tool path. The tensile specimens 2a, 2b and 2c are oriented at 30 degrees, 45 degrees and 60 degrees, respectively, with respect to the tool path direction. One or multiple tool path geometries may be explored within a single build of the Z-axis test coupon structure 1.

The geometry of the Z-axis test coupon structure 1 may serve several functions. One function may be to replicate the layered pattern of any part built concurrently in the FDM process. The arched or notched geometry of the upper web 16 and/or the lower web 22 connecting tensile specimens 2 may act as a self-supporting feature to eliminate the need for support material to be constructed for the grouping of the tensile specimens 2. Without the arched or notched feature, the requirement for support material may otherwise increase the estimated build time. In addition, by eliminating the need for support material, each tensile specimen 2 may require 45% less material than may otherwise be required.

The connecting arched geometry of the upper web and/or the lower web 22 of the Z-axis test coupon structure 1 may also act as a rigid body for the construction of the tensile specimens 2 to prevent a tensile specimen 2 from toppling over during building due to the vibrations which may be induced during the additive manufacturing process. In addition, this rigid body may also prevent the vibration inherent within the FDM process from manifesting itself as rough surfaces within the neck of each tensile specimen 2 during construction. As shown in FIG. 4, orientation text 13 may be provided on the lower grip 4 and/or the upper grip 5 of each tensile specimen 2. The orientation text 13 may define the relative position of each tensile specimen during construction and may assist in accurate recording of where the tensile specimen 2 is located within the grouping of tensile specimens 2.

By minimizing the use of support structure, the Z-axis test coupon structure 1 may significantly improve the build time of the tensile specimens 2. Moreover, by reducing vibration during fabrication, repeatability between multiple builds of tensile specimens 2 may be increased.

In FDM, each deposited layer may be a bonded, close-packed fibrous lamina, similar to fiber reinforced composites. Using the FDM bead width as a similarity to fiber orientation of classic laminate theory, the material properties may be defined along the fiber, or, x-direction and perpendicular to the fiber, or, y-direction. Each layer of a tensile specimen 2 may be similar to an individual ply in laminate theory.

Figure 5:
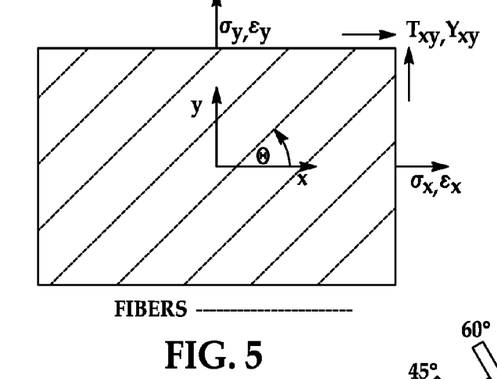
FIG. 5 is a fiber placement diagram illustrating placement of fibers in a single layer of a fused deposition modulus (FDM) structure.

Expounding on these observations and recognition of classic composite laminate theory, material properties may be listed relative to on-axis coordinates. Consider that the properties of an off-axis ply, anything other than 0 degrees, can be calculated by transforming the properties of the 0-degree ply. Let 0 be the x-axis, and note that the angle θ is measured from the x-axis to the 1-axis and is positive in the counterclockwise direction; the y-axis is perpendicular to the x-axis and in the plane of the ply, as in FIG. 5. All subsequent calculations may be made using the x-y, or laminate axes; therefore, it may be necessary to transform the stress-strain law from the material axes to the laminate axes. If the stresses in the laminate axes are denoted by $\sigma_x$, $\sigma_y$, and $\tau_{xy}$, then these may be related to the stresses referred to the material axes by the usual transformation equations, $$\begin{bmatrix} \sigma_x \\ \sigma_y \\ \tau_{xy} \end{bmatrix} = \begin{bmatrix} c^2 & s^2 & -2cs \\ s^2 & c^2 & 2cs \\ cs & -cs & c^2 - s^2 \end{bmatrix} \begin{bmatrix} \sigma_1 \\ \sigma_2 \\ \tau_{12} \end{bmatrix} \quad (1)$$

where c denotes cos θ and s denotes sin θ. Also, the strains in the material axes may be related to those in the laminate axes, namely, $\epsilon_x$, $\epsilon_y$, and $\gamma x_{xy}$, by what is essentially the strain transformation:

$$\begin{bmatrix} \varepsilon_1 \\ \varepsilon_2 \\ \gamma_{12} \end{bmatrix} = \begin{bmatrix} c^2 & s^2 & cs \\ s^2 & c^2 & -cs \\ -2cs & 2cs & c^2 - s^2 \end{bmatrix} \begin{bmatrix} \varepsilon_x \\ \varepsilon_y \\ \gamma_{xy} \end{bmatrix} \quad (2)$$

Figure 6:
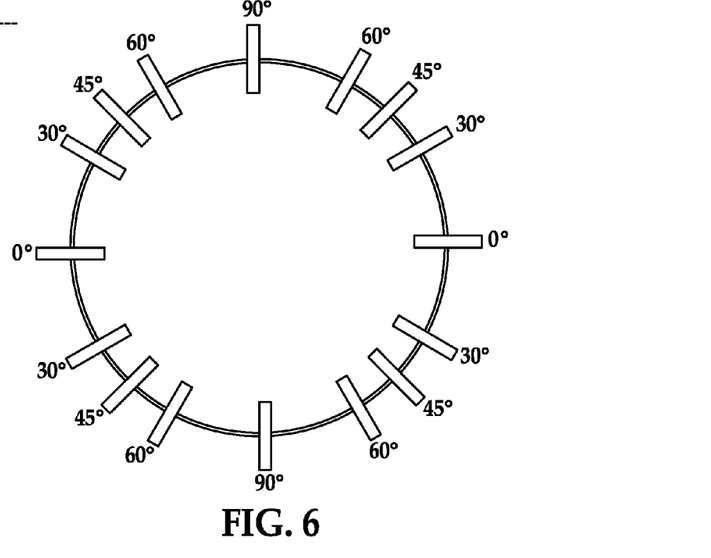
FIG. 6 is a diagram illustrating a multi-directionally loaded raster orientation of tensile specimens.

Consider a similar approach using FDM whereas the tensile specimen highlighted in FIG. 1 is shown in top view in FIG. 6. Raster orientations may be additively constructed in the FDM process. Therefore, each ply in composite laminate theory may be thought of as a raster pattern layer in the FDM process and by specifying each layers orientation to 0° each ply, or layer, the specimen may be defined to serve as a function of loading for multi-directionally loaded parts.

Each tensile specimen 2 may offer unique orientations to correlate to the laminate theory fundamental principles listed above. By tailoring several orientations within the same tensile specimen 2 in a circular pattern, the tensile specimen shown in FIG. 6 represents a multi-directionally loaded part. From a testing perspective, each multi-directionally loaded tensile specimen 2 may yield the following quantity of tensile bars or specimens listed in Table I below. By gaining raster orientation direction mechanical property data relative to the Z axis, a thorough knowledge capture may be attained for the FDM process.

TABLE I

Test Specimen for Multi-Directional Loaded Geometry

| | Quantity of Tensile Bars Per Specimen |
|---|---|
| 0° | 2 |
| 90° | 2 |
| 30° | 4 |
| 45° | 4 |
| 60° | 4 |

It may also be considered that if a design engineer designed a part to only take loads solely in a unidirectional format, an alternative tensile specimen configuration may be required. In such a situation, a raster pattern layout with all rasters constructed at 0° shown in FIG. 7 may be appropriate to simulate the functional unidirectional loading requirement. Using a unidirectional design requirement may yield a different configuration and quantity of tensile specimens as shown below in Table II.

TABLE II

Test Specimen for Uni-Directional Loaded Geometry

| | Quantity of Tensile Bars Per Specimen |
|---|---|
| 0° | 16 |
| 90° | 0 |
| 30° | 0 |
| 45° | 0 |
| 60° | 0 |

In summary, for FDM, the orientation of the raster pattern may be tailored to the specific design function needs required by the design engineer. These tensile specimens 2 may then be constructed concurrently with the production part and tested to ensure that product performance has been established. However, before any part is produced for production, the process may be optimized for structural integrity.

The second stage in the development of performance of FDM may include a thorough optimization effort to maximize the mechanical property performance of the Z direction. In parameter design, the engineer may select an effective characteristic to measure as data. Quality problems may take place because of variability in the energy transformation. Using FDM as an example, the process may be broken down to include an investigation of several parameters that influence mechanical property performance in the Z axis direction.

Mechanical property variability for the Fused Deposition Modeling process has been researched extensively. Several energy transfer parameters inherent to the FDM process may include raster orientation, raster air gap, bead width, and build temperature. Build temperature may become unavailable to users of newer FDM technology. Build temperature may be automatically controlled via a microchip material canister. Despite this restriction, bead width, raster orientation, and raster air gap may remain available to be adjusted by the end user.

Figures 7, 8, 9:
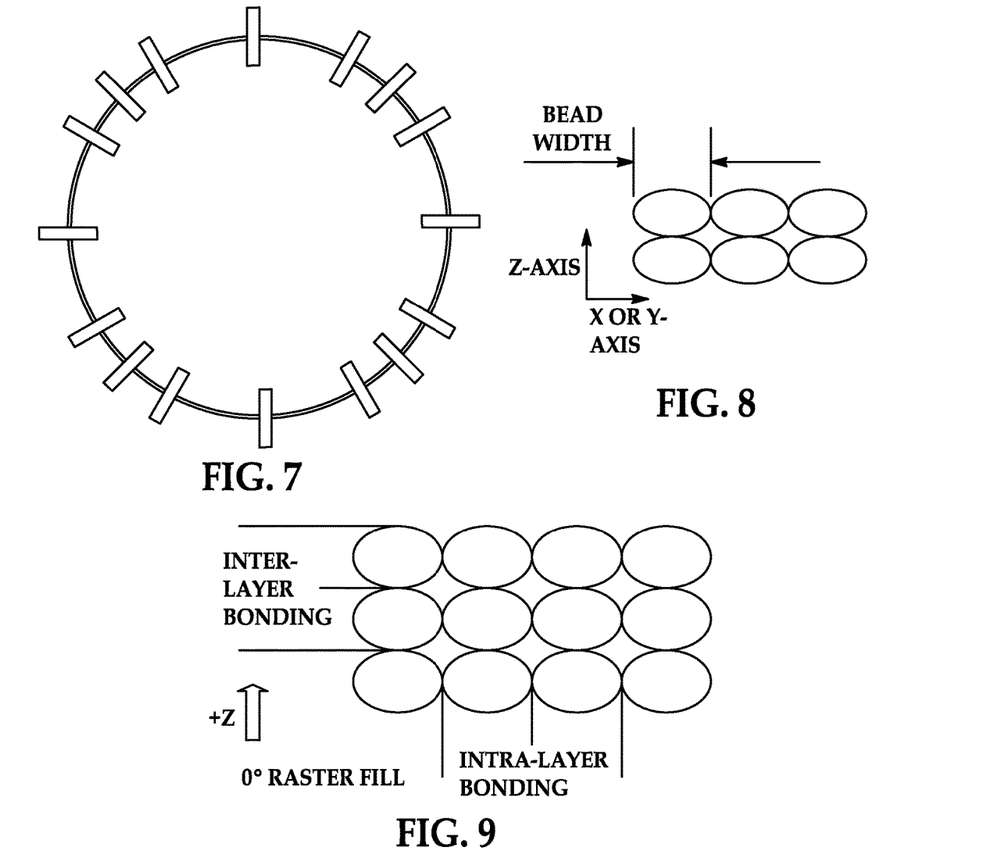
FIG. 7 is a diagram illustrating a uni-directionally loaded raster orientation of tensile specimens.
FIG. 8 is a diagram illustrating fused deposition modeling bead width.
FIG. 9 is diagram illustrating a 0° raster pattern.

The bead width may be dictated by the FDM user to provide a width to the toolpaths taken by the process. Two types of bead width are contour and raster. The contour is the outside wall of an X-Y sliced plane. The raster is the filled pattern inside the contour. FIG. 8 illustrates the bead width cross section 34 of a raster pattern 35. FIG. 9 is diagram 36 illustrating a 0° raster pattern 37.

Figure 11:
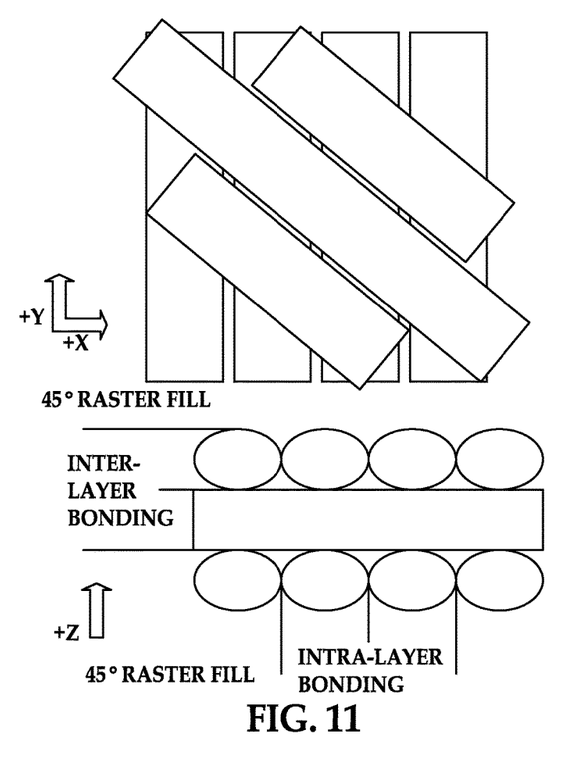
FIG. 11 is a diagram illustrating a 45° raster pattern.

Raster angle may be defined as the relative angle placement of contours in the Z direction. If a cross section were taken of a tensile specimen 2 in the Z direction FIG. 11 would highlight a 0°, 90°, 45° raster 41 orientation pattern 40 respectively.

Figure 10:
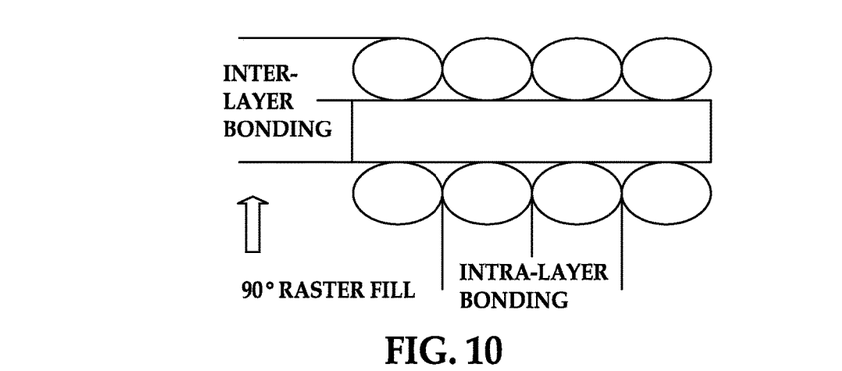
FIG. 10 is a diagram illustrating a 90° raster pattern.

The next parameter allowed for adjustment may be the perimeter to raster air gap. This feature may be defined as the amount of bead overlap between the interior fill material and the outside contour of a planar cross section. By lowering the airgap value, the user may create more overlap and reduce the voids between the raster pattern and the outside contour. FIG. 10 illustrates a build plane cross-sectional cut 38 of a piece of geometry reflecting perimeter to raster air gap.

Figure 12:
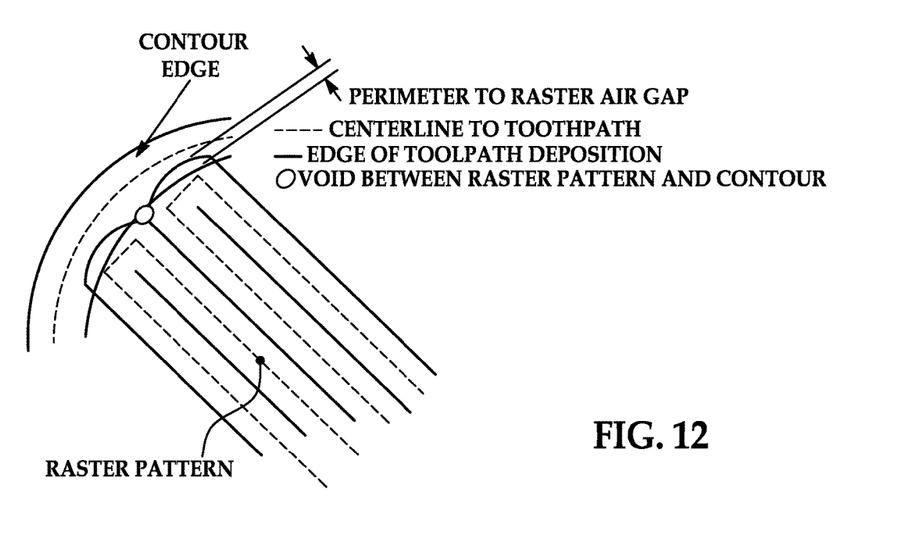
FIG. 12 is a diagram illustrating a perimeter to raster air gap.
Figures 13, 14:
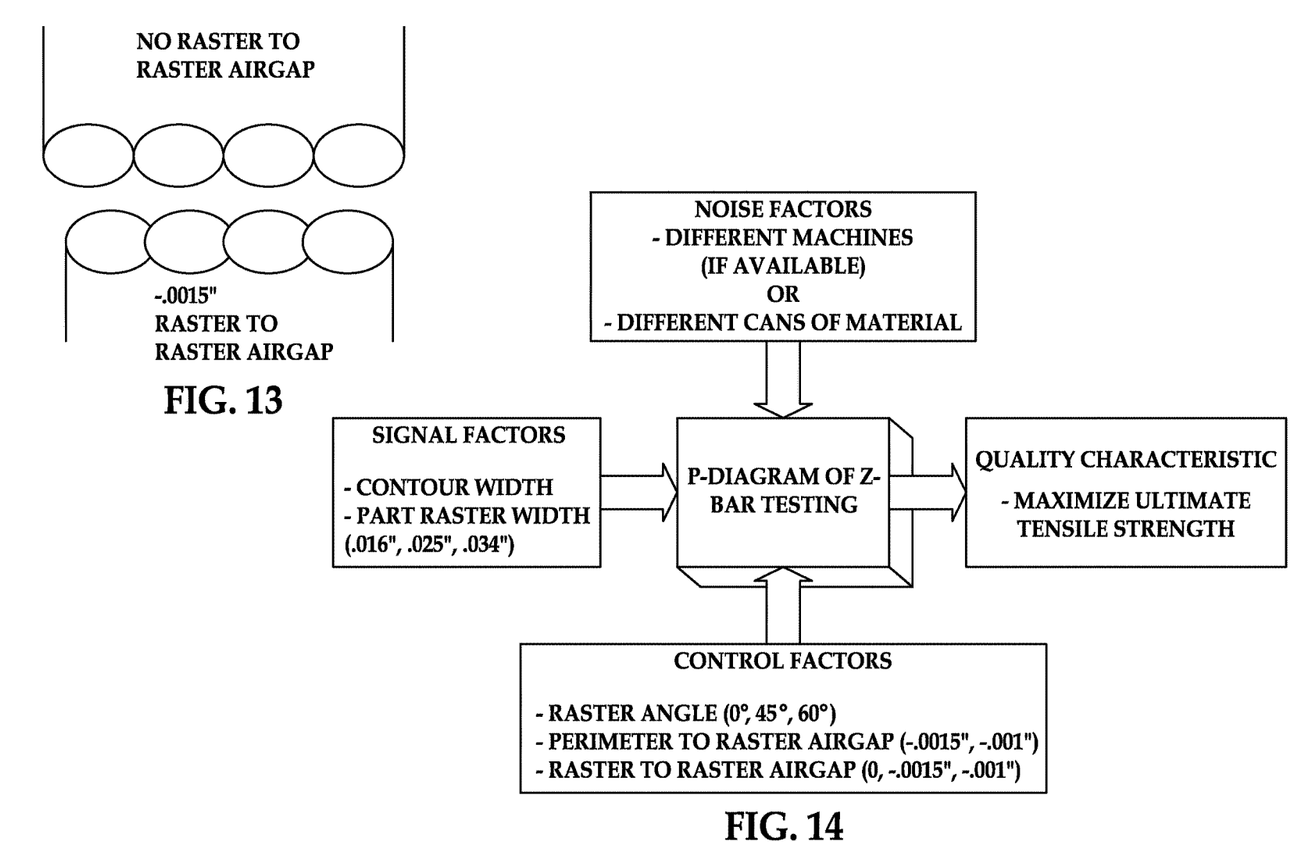
FIG. 13 is a diagram illustrating a raster to raster air gap.
FIG. 14 is a sample P-diagram for fused deposition modeling.

A third parameter allowed for adjustment may include raster to raster air gap. This factor may be defined as the amount of interstitial bonding among horizontal fill rasters. By reducing the raster to raster airgap, more overlap may create fewer voids in the process. If the airgap is reduced too much, then backpressure may occur in the deposition process and result in clogged deposition tips. FIG. 12 illustrates raster to raster airgap 44. FIG. 13 illustrates a no raster to raster airgap configuration 46 juxtaposed with a raster to raster airgap configuration 47.

It has been noted in industry that if several FDM machines are used for production, each may need parameter adjustments to reduce the amount of variation that exists within the process to consistently produce direct parts that exhibit similar mechanical properties. Using the known parameters, a planned Design of Experiment (DOE) may be conducted to determine the appropriate settings for maximum mechanical properties in the Z direction. An expansive list of research has been completed regarding the use of Designed Experimentation for FDM, specifically the popular Taguchi method. The objective of this research is to simply introduce the audience to steps involved for appropriate technology optimization, for more detailed information regarding Designed Experiments consult Fowlkes and Creveling (1995).

The first step of a planned DOE shall be the development of a P-Diagram. FIG. 14 offers a P-Diagram example 57 that may be used as a model for FDM testing. The P-diagram of Z-bar testing 57 may include noise factors 54 (different machines, different cans of material), signal factors 55 (contour width, part raster width) and control factors 56 (raster angle, perimeter to raster airgap, raster to raster airgap) which are used to determine a quality characteristic (maximum ultimate tensile strength 58. From this point, a partial orthogonal array may be used to develop an effective control factor effect plot of each of the control factors to determine their levels of influence to the overall system. Based on applied research, Taguchi method of Robust Design may include development of a P-Diagram 57, choose an orthogonal array to represent the FDM tensile bar layout, run a static controlled experiment and conduct an analysis of means (ANOM) to determine the appropriate combination of parameters that results in the highest tensile strength 58.

Next, in order to understand variation within the system, another partial arrayed experiment and tensile test may be conducted to capture Signal to Noise ratio as the metric for system variation. Because the tensile properties are to be maximized, the larger-the-better S/N ratio may be used and illustrated below:

$$S/N_{LTB} = -10\log[MSD] = -10\log\left[\frac{1}{n}\sum_{i=1}^{n}\left(\frac{1}{y_i^2}\right)\right]$$

Whereas MSD is the mean squared deviation of data, n is the number of samples and $y_i$ are the individually measured response values squared to increase or bias the impact of any large y values.

Upon determining the S/N, the next step may be to perform an analysis of variation (ANOVA) to determine overall system robustness. ANOVA may use a mathematical technique known as the sum of squares to quantitatively examine the deviation of the control factor effect response averages from the experimental mean response. Using ANOVA, the process may be understood to gain knowledge into which control factors are of higher criticality and which are of lesser importance.

To begin the ANOVA process, one may calculate the grand total sum of squares (GTSS). This may be calculated by the following:

$$GTSS = \sum_{i=1}^{9}(S/N)_i^2$$

Once computed, an error variance estimating may be conducted and F-ratio testing may be analyzed to test for significance of factor effects. Upon completion of the ANOVA test, data may be analyzed to determine which factors contribute to the overall variance of the process. This information may be helpful to develop an optimization plan for the process.

Once the FDM system is optimized for Z axis properties, a database of tensile properties may exist to aid design engineers in making decisions regarding performance of FDM. Known in industry as design allowables, these data may offer substantiation for candidate parts to perform in relative operational conditions. The larger the database, the more credibility may be added for AM to act as a legitimate manufacturing process. Finite Element Analysis packages may generally allow for isotropic property input for modulus; therefore, the design engineers may use Z axis modulus data to determine a worst-case condition for operating usage environments.

Figure 15:
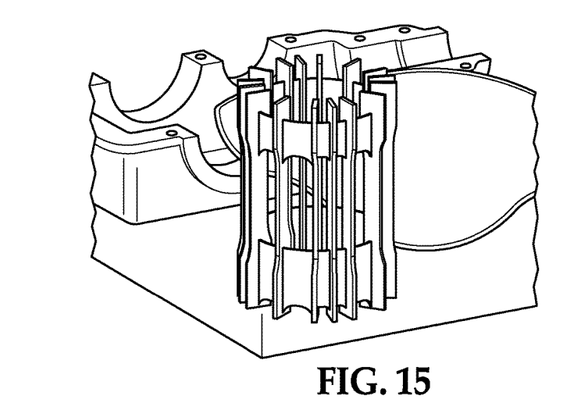
FIG. 15 is a perspective view of a fused deposition modeling tensile specimen nested within build volume.

Next, candidate parts may be selected to exploit the FDM process. The tensile specimen 2 may be placed within the build volume as shown in FIG. 15. Each tensile specimen 2 may offer a unique build pattern to match closely to a part fabricated in the FDM process. This build pattern may allow for part geometry to be constructed with most feature definition simulated via tensile specimen grouping with the test geometry shown in FIG. 15.

Once a representative part is constructed within a build volume as depicted in FIG. 15, the tensile specimen 2 may be removed from the build chamber, broken into individual tensile specimens 2 and tensile tested per ASTM D638 conditioning. Data may be analyzed to provide a clear understanding of the range of raster orientations contribution to Z axis tensile strength. As shown in FIG. 2, the tensile specimens 2 may be separated from each other by forming web breaks 19 in the upper web 16 and/or the lower web 22.

Part candidate selection may go hand-in-hand with mechanical property evaluation. These parts may be generally highly complex, low quantity geometries that may be polymer-based. These parts may be difficult to construct using conventional manufacturing solutions. In addition, assembly integration, or the ability to combine several parts into a single part, may be taken into account during part selection.

Once parts are selected, correct identification of appropriate parts that can/could be manufactured may be necessary. There may be parts that are suitable for AM, parts that are competitive with conventional techniques and some parts that can only be manufactured additively—it is these last two categories that may be pursued, but a robust methodology for identifying these applications may be investigated.

Figure 16:
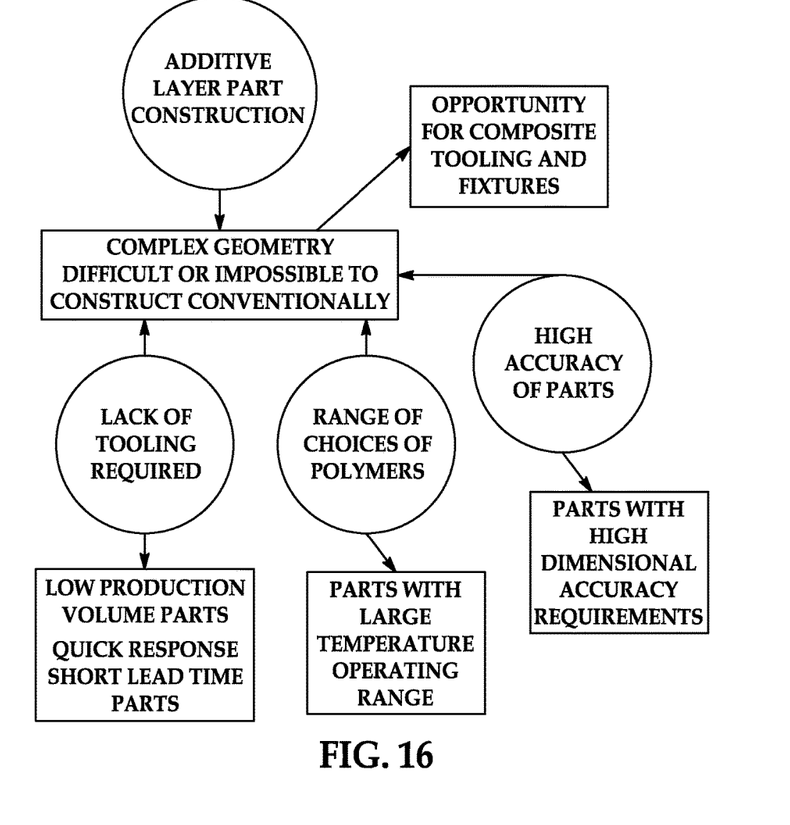
FIG. 16 is a block diagram illustrating elements of part candidate screening for fused deposition modeling.

A single part may not be compared among technologies without first leveraging the unique characteristics of the emerging manufacturing process. The main emergent technology trait of AM may be part design flexibility. Using FDM as element of AM, FIG. 16 shows the unique elements 61 of the FDM process 60 and what features of functional part candidates 62 may be an attractive trait for each element. For FDM, each element may share a common theme that leverages a need for complex geometry that is difficult or impossible to construct using conventional manufacturing technology. The target application, in the case of FDM, tooling and fixtures, may be generated from blending the elements aligned to the FDM technology.

Figure 17:
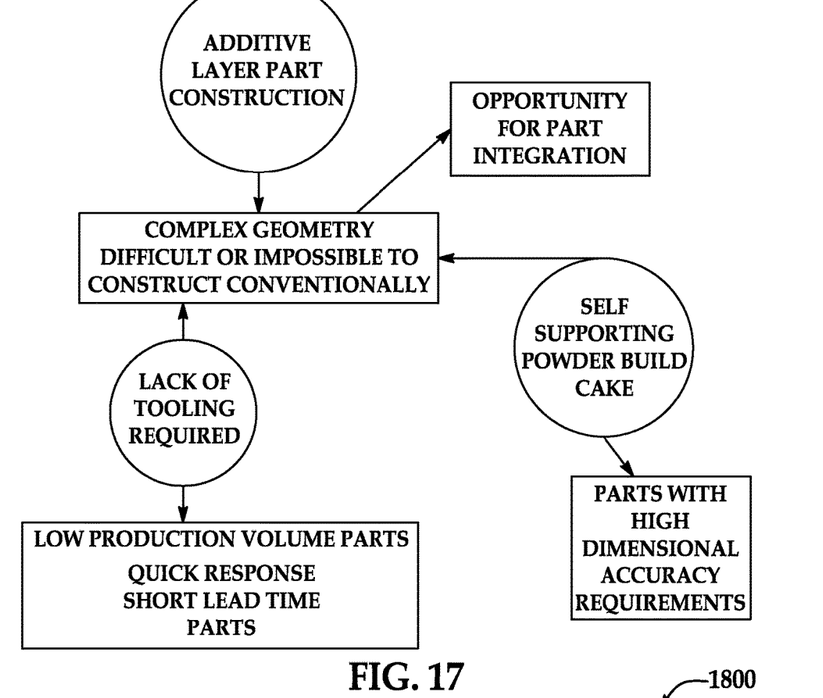
FIG. 17 is a block diagram illustrating elements of part screening for selective laser sintering.

Because SLS (Selective Laser Sintering) may be a separate AM technology than FDM, its fundamental process elements may be different than FDM; therefore, a different model may be constructed for SLS. SLS may be more aligned to encapsulated geometry; however, its material choices may be much more limited. Also, SLS may not be as accurate as FDM. However, SLS may offer an advantage in that its support mechanism for part construction may be self-supporting powder. Therefore, a snapshot of how SLS screening 64 with the various SLS components 65 may look is illustrated in FIG. 17. Due to its ability to build encapsulated geometry easily, SLS may offer the most design flexibility of comparative AM technologies and position itself for part integration opportunities.

Figure 17A:
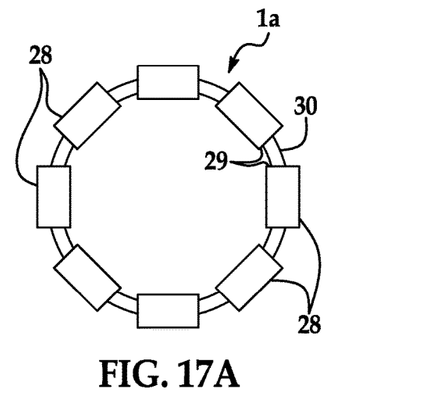
FIG. 17A is a top view of an alternative illustrative embodiment of the Z-axis test coupon structure.

Referring next to FIG. 17A, an alternative illustrative embodiment of the Z-axis test coupon structure is generally indicated by reference numeral 1a. The Z-axis test coupon structure 1a may be similar in design to the Z-axis test coupon structure 1 which was heretofore described with respect to FIGS. 1-4. In the Z-axis test coupon structure 1a, tensile specimens 28 may be connected to each other in edge-to-edge relationship in a circular configuration via at least one web 30 which connects the specimen edges 29 of the adjacent tensile specimens 28 to each other.

Figure 18:
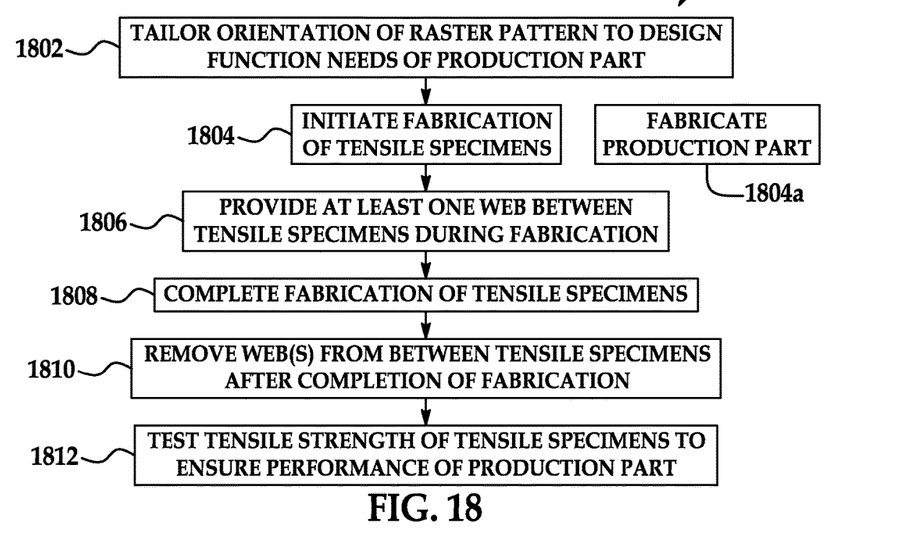
FIG. 18 is a flow diagram of an illustrative method of fabricating standardized Z-axis test coupons for additive manufacturing processes.

Referring next to FIG. 18, a flow diagram 1800 of an illustrative method of fabricating standardized Z-axis test coupons for additive manufacturing processes is shown. In block 1802, orientation of a raster pattern may be tailored to the design function needs of a part. In block 1804, fabrication of tensile specimens may be initiated. In block 1804a, the production part may be fabricated simultaneously. In block 1806, at least one web may be provided between the tensile specimens during fabrication. In block 1808, fabrication of the tensile specimens may be completed. In block 1810, the web or webs may be removed from between the tensile specimens after fabrication. In block 1812, the tensile strength of the tensile specimens may be tested to ensure performance of the production part.

Figure 19:
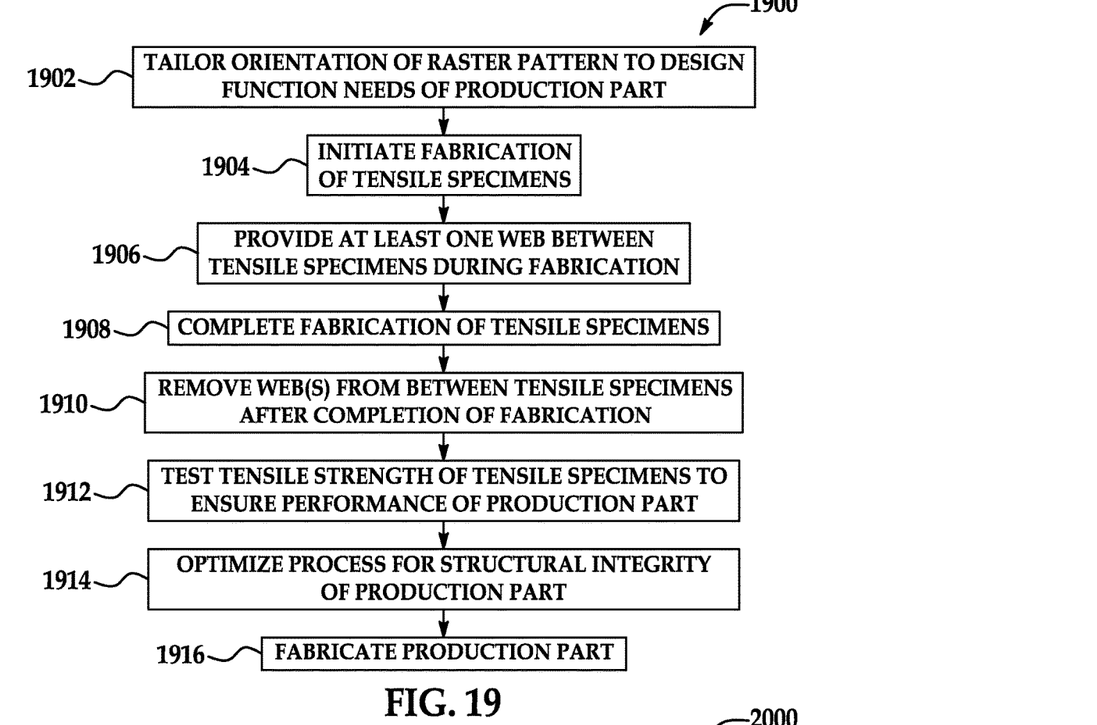
FIG. 19 is a flow diagram of an alternative illustrative method of fabricating standardized Z-axis test coupons for additive manufacturing processes.

Referring next to FIG. 19, a flow diagram 1900 of an alternative illustrative method of fabricating standardized Z-axis test coupons for additive manufacturing processes is shown. In block 1902, orientation of a raster pattern may be tailored to the design function needs of a part. In block 1904, fabrication of tensile specimens may be initiated. In block 1906, at least one web may be provided between the tensile specimens during fabrication. In block 1908, fabrication of the tensile specimens may be completed. In block 1910, the web or webs may be removed from between the tensile specimens after fabrication. In block 1914, the tensile strength of the tensile specimens may be tested to ensure performance of the production part. In block 1916, the production part may be fabricated after optimization in block 1914.

Figure 20:
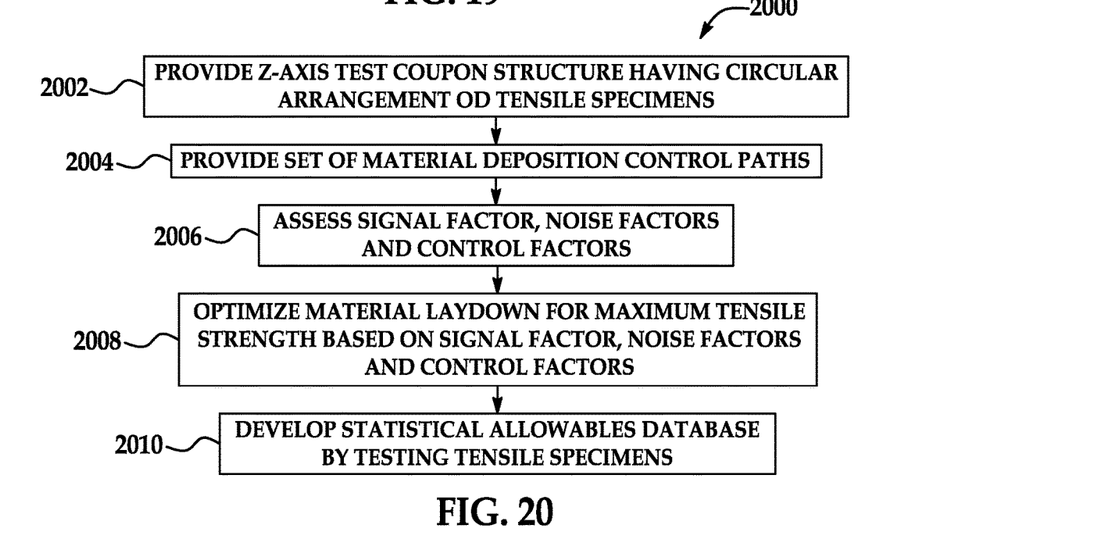
FIG. 20 is a flow diagram of an illustrative method of developing consistent material allowables for additive manufacturing using Design of Experiments (DOE).

Referring next to FIG. 20, a flow diagram 2000 of an illustrative method of developing consistent material allowables for additive manufacturing using Design of Experiments (DOE) is shown. In block 2002, a Z-axis test coupon structure having a circular arrangement of tensile specimens may be provided. In block 2004, a set of material deposition control paths may be provided. In block 2006, signal factors, noise factors and control factors of the Z-axis coupon structure may be assessed. In block 2008, material laydown for maximal tensile strength of a production part may be optimized based on the signal factor, the noise factors and the control factors. In block 2010, a statistical allowables database may be developed by testing the tensile specimens.

Figure 21:
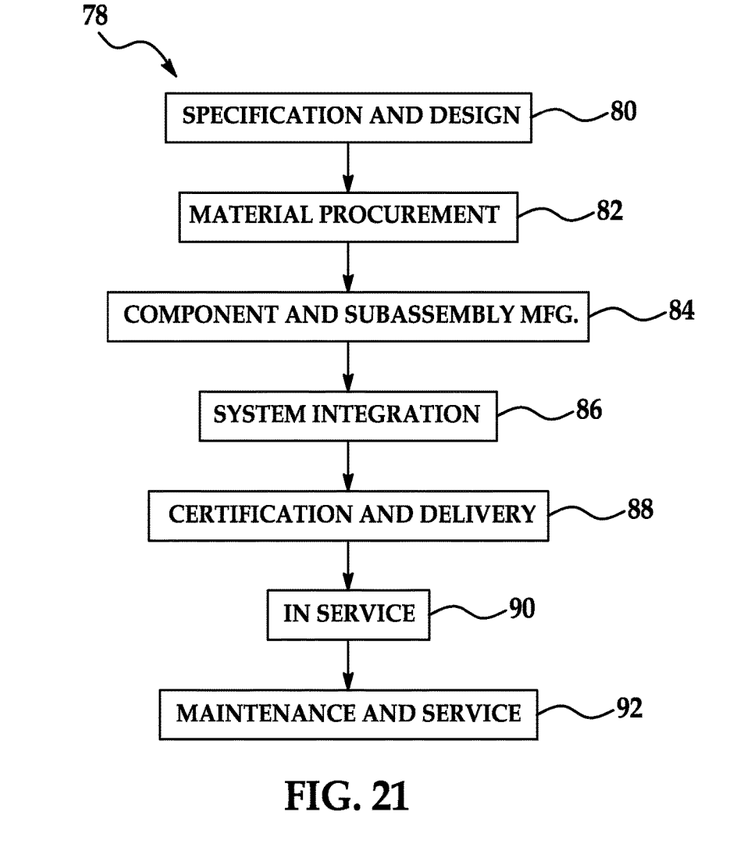
FIG. 21 is a flow diagram of an aircraft production and service methodology.
Figure 22:
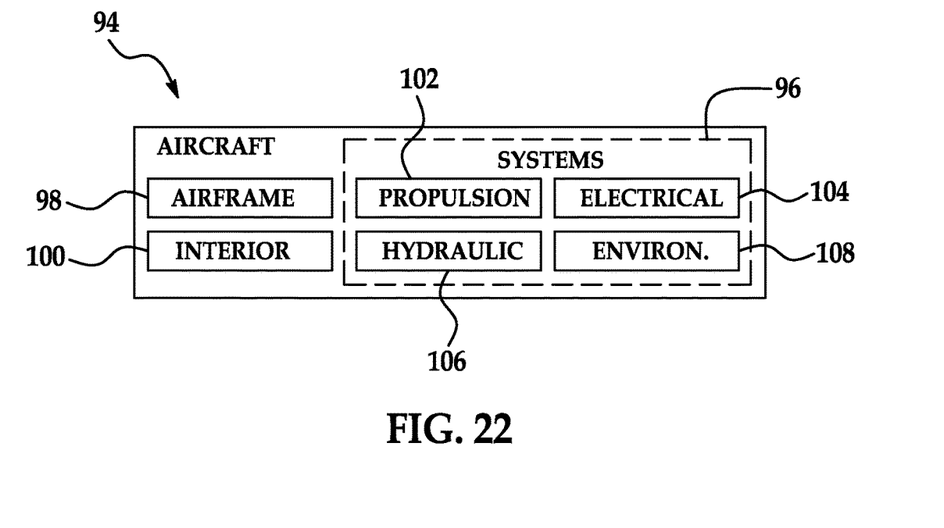
FIG. 22 is a block diagram of an aircraft.

Referring next to FIGS. 21 and 22, embodiments of the disclosure may be used in the context of an aircraft manufacturing and service method 78 as shown in FIG. 21 and an aircraft 94 as shown in FIG. 22. During pre-production, exemplary method 78 may include specification and design 80 of the aircraft 94 and material procurement 82. During production, component and subassembly manufacturing 84 and system integration of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 22, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of this disclosure may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method, comprising:
   fabricating tensile specimens, the fabricating of the tensile specimens including providing a web between adjacent ones of the tensile specimens, and the fabricating of the tensile specimens including using an additive manufacturing process;
   removing the web from between the adjacent ones of the tensile specimens; and
   testing a tensile strength of one of the tensile specimens;
   wherein the fabricating of the tensile specimens comprises circumferentially spacing the tensile specimens about a shape having a center on a first axis such that respective longitudinal axes of the tensile specimens are parallel to the first axis.

2. A method as defined in claim 1, further comprising defining a tool path orientation in the tensile specimens, the fabricating of the tensile specimens being based on the tool path orientation.

3. A method as defined in claim 1, further comprising fabricating a production part simultaneously with the fabricating of the tensile specimens.

4. A method as defined in claim 1, further comprising optimizing the testing of the tensile strength of the one of the tensile specimens.

5. A method as defined in claim 4, further comprising fabricating a production part based on the optimizing of the testing.

6. A method as defined in claim 1, wherein the providing of the web between the adjacent ones of the tensile specimens comprises constructing the web to have a flat upper edge and a notched lower edge.

7. A method as defined in claim 6, wherein the web is an upper web, the method further comprising providing a lower web between the adjacent ones of the tensile specimens, the lower web having a flat upper edge and a notched lower edge.

8. A method as defined in claim 1, wherein the fabricating of the tensile specimens comprises fabricating a first one of the tensile specimens to have an elongated middle section and to have a lower grip and an upper grip provided at respective ends of the middle section.

9. A method as defined in claim 1, further comprising:
   developing a statistical allowables database for a production part based on the testing of the tensile specimens.

10. A method as defined in claim 9, further comprising:
    assessing at least one of a signal factor, a noise factor, or a control factor of the tensile specimens; and
    optimizing material laydown for maximum tensile strength of the production part based on the at least one of the signal factor, the noise factor, or the control factor.

11. A method as defined in claim 9, wherein the developing of the statistical allowables database comprises determining a worst-case condition for operating usage environments for the production part based on the testing of the tensile specimens.

12. A method as defined in claim 1, wherein the first axis is vertical.

13. A method as defined in claim 1, wherein fabricating of the tensile specimens comprises orienting the tensile specimens at different respective angles with respect to at least one tool path direction.

14. A method as defined in claim 1, wherein the fabricating of the tensile specimens includes using a fused deposition modeling process.

* * * * *